United States Patent
Jin et al.

(10) Patent No.: US 10,815,416 B2
(45) Date of Patent: Oct. 27, 2020

(54) MULTI-FUNCTIONAL SURFACTANT SOLUTION FOR IMPROVING HYDROCARBON RECOVERY

(71) Applicant: Alchemy Sciences, Inc., Houston, TX (US)

(72) Inventors: Luchao Jin, Houston, TX (US); James Russum, Sugar Land, TX (US)

(73) Assignee: ALCHEMY SCIENCES, INC., Houston, TX (US)

( * ) Notice: Subject to any disclaimer, the term of this patent is extended or adjusted under 35 U.S.C. 154(b) by 86 days.

(21) Appl. No.: 16/379,367

(22) Filed: Apr. 9, 2019

(65) Prior Publication Data

US 2019/0309216 A1    Oct. 10, 2019

Related U.S. Application Data (60) Provisional application No. 62/654,994, filed on Apr. 9, 2018.

(51) Int. Cl.
  *C09K 8/60* (2006.01)
  *C09K 8/80* (2006.01)
  (Continued)

(52) U.S. Cl.
  CPC .......... *C09K 8/602* (2013.01); *C09K 8/80* (2013.01); *E21B 43/267* (2013.01); *G01N 33/2823* (2013.01)

(58) Field of Classification Search
  CPC ........ E21B 43/267; E21B 43/16; E21B 43/26; C09K 8/602; C09K 8/80; C09K 8/665; C09K 8/68; C09K 8/88; G01N 33/2823
  See application file for complete search history.

(56) References Cited

U.S. PATENT DOCUMENTS 10,266,750 B2 * 4/2019 Oghena .............. C09K 8/588
2007/0215347 A1  9/2007 Tang
(Continued)

FOREIGN PATENT DOCUMENTS

WO    2018017482 A1    1/2018

OTHER PUBLICATIONS

International Search Report and Written Opinion issued in Application No. PCT/US2019/026588, dated Jul. 5, 2019, 8 pages.

*Primary Examiner* — Daniel P Stephenson
(74) *Attorney, Agent, or Firm* — Adolph Locklar (57) ABSTRACT

A fluid injection process includes removing a core sample from a low permeability reservoir. The process also includes performing an imbibition test on a plurality of stage one surfactants, each stage one surfactant mixed with a first treatment fluid, using a portion of the core sample to obtain a wettability index or measurement of capillary pressure for each stage one surfactant. In addition, the process includes selecting a stage one surfactant by determining which of the plurality of stage one surfactants has the highest wettability index or lowest capillary pressure and performing an oil recovery test on a plurality of stage two surfactants, each stage two surfactant mixed with a second treatment fluid. Further, the process includes selecting a stage two surfactant by determining which of the plurality of stage two surfactants has the highest oil recovery test result and injecting the selected stage one surfactant into a matrix of the low permeability reservoir. In addition, the method includes injecting the selected stage two surfactant into a fracture network of the low permeability reservoir.

14 Claims, 5 Drawing Sheets

(51) Int. Cl.
  *E21B 43/267* (2006.01)
  *G01N 33/28* (2006.01)

(56) References Cited

U.S. PATENT DOCUMENTS

| | | | |
|---|---|---|---|
| 2012/0292025 A1* | 11/2012 | Stoll | E21B 43/16 |
| | | | 166/269 |
| 2015/0114635 A1* | 4/2015 | Ovalles | C10G 73/38 |
| | | | 166/263 |
| 2016/0215202 A1 | 7/2016 | Weaver et al. | |
| 2016/0377521 A1* | 12/2016 | Wickramathilaka | G01N 13/02 |
| | | | 73/38 |
| 2017/0030819 A1 | 2/2017 | McCarty et al. | |
| 2017/0292375 A1 | 10/2017 | Feng et al. | |
| 2018/0362842 A1* | 12/2018 | Bello | C09K 8/602 |
| 2019/0309216 A1* | 10/2019 | Jin | C09K 8/602 |
| 2020/0173975 A1* | 6/2020 | Cinar | G01N 13/00 |

* cited by examiner

MULTI-FUNCTIONAL SURFACTANT SOLUTION FOR IMPROVING HYDROCARBON RECOVERY

This application is a non-provisional application which claims priority from U.S. provisional application No. 62/654,994, filed Apr. 9, 2018 which is incorporated herein in its entirety.

BACKGROUND

Field

The disclosure relates generally to the field of treatment fluids used in fracturing subterranean formations during hydrocarbon recovery. More specifically the disclosure relates to methods for selecting surfactants used in treatment fluids.

Background Art

Recovery of hydrocarbons from low permeability reservoirs may be difficult. Hydrocarbons in such low permeability reservoirs may be held within a matrix of small pores. The permeability of this matrix may be quite low, often less than one millidarcy. Hydraulic fracturing is a formation stimulation technique used to create additional permeability in a low permeability reservoir to increase the flow of hydrocarbons toward a wellbore. Typically, during a hydraulic fracturing operation, a high hydraulic pressure treatment fluid (referred to herein as a "treatment fluid") is used to fracture the formation, creating hydraulic fractures that facilitate the increased flow of hydrocarbons from the low permeability reservoir. The hydraulic fractures and naturally occurring microfractures may then transport the hydrocarbon to the wellbore. Proppants may be used to keep the hydraulic fractures and the naturally occurring microfractures open that were created during the fracturing operation.

Treatment fluids include a number of components and are most often water-based. These components typically include acids, biocides, breakers, corrosion inhibitors, friction reducers, gels, iron control chemicals, oxygen scavengers, surfactants and scale inhibitors. The treatment fluid in combination with the hydrocarbon may flow from the matrix to the hydraulic fractures and naturally occurring microfractures. The treatment fluid and hydrocarbons may then flow from the hydraulic fractures and naturally occurring microfractures to the wellbore.

The surfactant in the treatment fluid may act to increase productivity from low permeability reservoirs, such as by enhancing water imbibition into the matrix and aiding oil flow from the hydraulic fractures and naturally occurring microfractures to the wellbore. Selection of a surfactant for the treatment fluid may be determined by a number of factors, including, but not limited to wettability, interfacial surface tension, ability to emulsify, and compatibility with other components of the treatment fluid. Traditionally, a single surfactant or single mixture of surfactants is used in the treatment fluid to facilitate both enhanced imbibition and aiding oil flow.

SUMMARY

A fluid injection process is disclosed. A fluid injection process includes removing a core sample from a low permeability reservoir. The process also includes performing an imbibition test on a plurality of stage one surfactants, each stage one surfactant mixed with a first treatment fluid, using a portion of the core sample to obtain a wettability index or measurement of capillary pressure for each stage one surfactant. In addition, the process includes selecting a stage one surfactant by determining which of the plurality of stage one surfactants has the highest wettability index or lowest capillary pressure and performing an oil recovery test on a plurality of stage two surfactants, each stage two surfactant mixed with a second treatment fluid. Further, the process includes selecting a stage two surfactant by determining which of the plurality of stage two surfactants has the highest oil recovery test result and injecting the selected stage one surfactant into a matrix of the low permeability reservoir. In addition, the method includes injecting the selected stage two surfactant into a fracture network of the low permeability reservoir.

A method of performing a hydraulic fracturing operation is disclosed. The method includes hydraulically isolating a portion of a well and injecting a first treatment fluid without proppant into the hydraulically isolated portion of the well, the first treatment fluid including a stage one surfactant. In addition, the method includes adding proppant to the first treatment fluid and injecting a second treatment fluid without proppant into the hydraulically isolated portion of the well, the second treatment fluid including a stage two surfactant.

BRIEF DESCRIPTION OF THE DRAWINGS

The present disclosure is best understood from the following detailed description when read with the accompanying figures. It is emphasized that, in accordance with the stand practice in the industry, various features are not drawn to scale. In fact, the dimensions of the various features may be arbitrarily reduced for clarity of discussion.

DETAILED DESCRIPTION

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Further, various ranges and/or numerical limitations may be expressly stated below. It should be recognized that unless stated otherwise, it is intended that endpoints are to be interchangeable. Further, any ranges include iterative ranges of like magnitude falling within the expressly stated ranges or limitations. For example, if the detailed description recites a range of from 1 to 5, that range includes all iterative ranges within that range including, for instance, 1.3-2.7 or 4.9-4.95.

The present disclosure relates to methods for treating and treatment fluids for low permeability reservoirs. As used herein, "low permeability reservoir" is defined to any reservoir having a matrix permeability of less than 500 millidarcies (mD). A non-limiting example of a low permeability reservoir is an oil-containing shale formation. As used herein, "shale" may refer to a fine grain reservoir such as a mudstone, siltstone, or limey mudstone.

Processes in which such treatment fluids may be used may include, but are not limited to, hydraulic fracturing treatments, enhanced oil recovery treatments (including, for instance, water flooding treatments and polymer flooding treatments), acidizing treatments, and drilling. In certain embodiments, the low permeability reservoir may be contacted by the treatment fluid, such as, for instance, introduction into a well bore that penetrates the low permeability reservoir.

The present disclosure includes tests that may be performed to select surfactants for treatment fluids. In certain embodiments, both tests are used. In other embodiments, one of the tests may be performed. These tests may be performed in any order and the order described below is non-limiting. Further, other tests may be used that are not delineated below.

Figure 1:
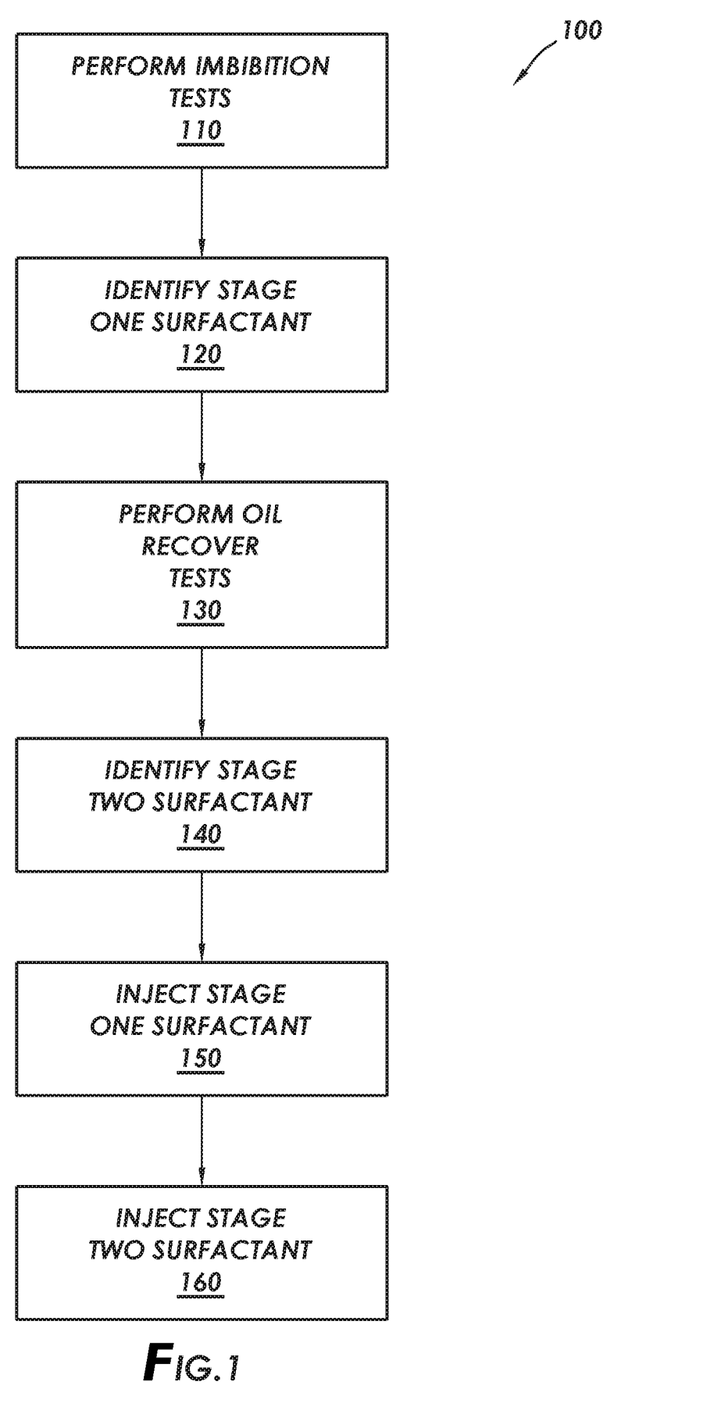
FIG. 1 is flowchart depicting a treatment fluid injection process consistent with certain embodiments of the present disclosure

FIG. 1 is flowchart depicting treatment fluid injection process 100 consistent with certain embodiments of the present disclosure. In the embodiment shown in FIG. 1, treatment fluid injection process 100 includes perform imbibition tests 110.

During a hydraulic fracturing operation, millions of gallons of water may be pumped into the low permeability reservoir. Because of the low permeability and nanometer-sized pores in the low permeability reservoir, water may display high capillary pressure and imbibe into the pores. Without being bound by theory, if the formation pressure of the low permeability reservoir is lower than the capillary pressure of invaded water, the water may plug the pores of the matrix and the oil or gas cannot flow when the well is put on production. In the presence of certain stage one surfactants, the high capillary pressure of invaded water may be reduced and the water may be returned together with oil and gas, thereby reducing formation damage/plugging and enhancing production. "Stage one surfactant" as used herein refers to a surfactant selected to enhance release of hydrocarbons from the matrix.

The ability of a stage one surfactant to facilitate oil exiting the matrix may be determined by an imbibition test. An imbibition test may be used to determine the ability of an aqueous phase to displace a hydrocarbon phase in a reservoir sample. One technique for such determination is the Amott cell test, which is performed by immersing a sample of the porous media in an oil field brine and surfactant mixture and measuring the amount of mixture that the porous media imbibes or the amount of oil that is released from the sample. Other non-limiting examples include the USBM (U.S. Bureau of Mines) test, contact angle measurement, and measurement of the electrical resistivity of the rock to determine water saturation. Wettability is the ability of a fluid phase to preferentially wet a solid surface in the presence of a second immiscible phase. With respect to the low-permeability reservoir, wettability refers to whether the reservoir is water or oil wet. In certain embodiments, a core plug of the formation of the low permeability reservoir or disaggregated material from the formation of the low-permeability reservoir may be used in the imbibition test. The treating fluid containing a stage one surfactant may be used in the imbibition test.

Figure 2:
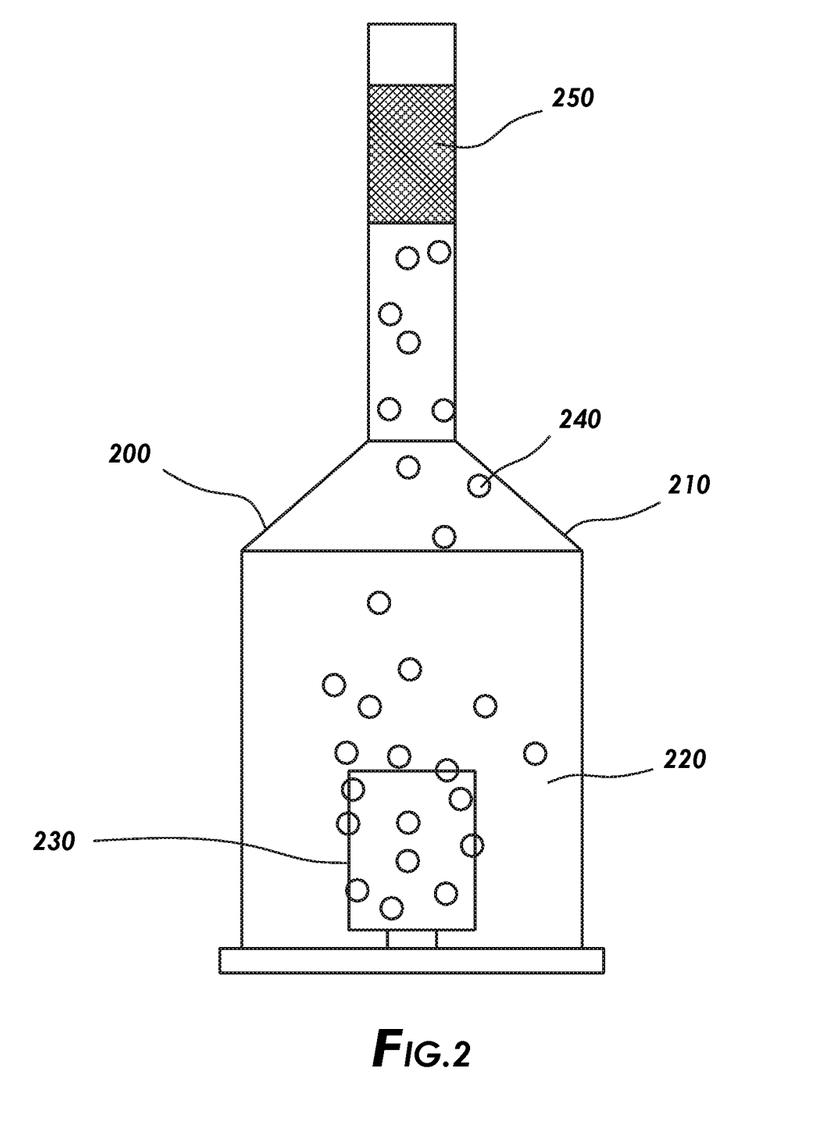
FIG. 2 is a depiction of a non-limiting example of an imbibition test apparatus consistent with certain embodiments of the present disclosure.

FIG. 2 is a depiction of Amott cell 200, used in a non-limiting example of a spontaneous imbibition test. The apparatus consists of a sealed, inverted glass vessel 210 which holds a core sample 230, with an integrated volumetric buret at the top. An aged and oil-saturated core sample 230 is placed in vessel 210, which is then submerged under a known volume of brine or brine/surfactant 220. Oil bubbles 240 are evolved from oil-saturated core sample 230. The volume of oil displaced 250 from the core by the imbibing fluid is then measured over time by reading the volume gradation on the integrated buret.

The imbibition tests conducted in FIG. 1 step 110 may result in a simple quantitative measurement of the volume of oil displaced 250, combined with forced imbibition test to yield a calculated wettability index (e.g., the Amott-Harvey Wettability Index), or a measurement of the capillary pressure. The test may be repeated for different imbibing fluids having different stage one surfactants.

In identify stage one surfactant 120, the imbibition test results from the imbibition tests in perform imbibition tests 110 are compared for the tested treatment fluids. In certain embodiments, the surfactant that has the highest imbibition test result may be selected as the stage one surfactant. In other embodiments, a predetermined threshold for the imbibition test result may be compared to the imbibition test results and only treatment fluids meeting the predetermined threshold may be identified as the stage one surfactant. In one non-limiting example, the threshold may be set based upon the economics of employing a surfactant. In such a case, the standard, or control, sample may be the core imbibed with brine only, without the addition of a surfactant. The amount of oil released spontaneously with brine only as compared to the amount of oil released with various surfactants may be determined. The incremental cost of adding a surfactant to the actual commercial recovery process may then be calculated.

As further depicted in FIG. 1, treatment fluid injection process 100 further includes perform oil recovery tests 130. In perform oil recovery tests 130, crushed formation cores may be saturated with crude oil from the formation of the low permeability reservoir and the treatment fluid containing a stage two surfactant is passed through the cores that are packed in a glass column. The stage two surfactant may be a single surfactant or a mixture of surfactants. Effluents are collected and oil recovery by each treatment fluid containing a stage two surfactant may be quantified.

Figure 3:
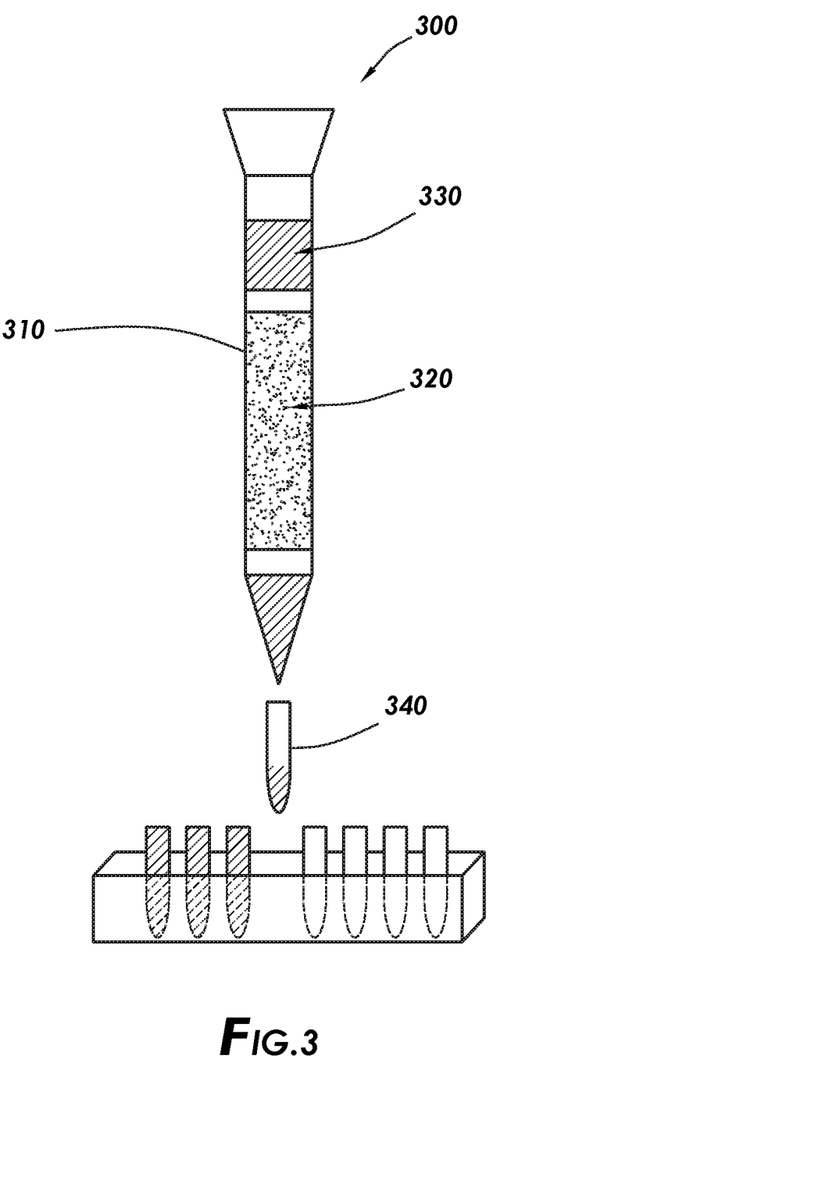
FIG. 3 is a depiction of an oil recovery column for an oil recovery test consistent with certain embodiments of the present disclosure.

FIG. 3 depicts oil recovery column 300, which includes glass column 310. Crushed formation cores 320 are placed within glass column 310. Subsequently, stage two surfactant 330 is poured into glass column 310 above crushed formation core 320. Effluent is collected in sample collectors 340. The oil recovery tests may be performed on a series of stage two surfactants.

Oil recovery tests measure the effectiveness of the stage two surfactant in enhancing flow through fractures and naturally occurring microfractures. Without being bound by theory, the stage two surfactant is retained within the combination of the fractures and naturally occurring microfractures, referred to herein as the "fracture network," which aids oil flow from the fracture network into the wellbore. Core plugs contain oil globules that are trapped inside the fracture network. It may not be feasible to pump the surfactant solution directly through a shale core plug because large differential pressure is required. In addition, the oil recovered from shale core plugs is typically so little that the results may not be reproducible. With the oil recovery test of the present disclosure, it is possible to differentiate the oil extraction capabilities by various stage two surfactants.

In identify stage two surfactant 140, the oil recovery test results from the oil recovery tests in perform oil recovery tests 130 are compared for the tested stage two surfactants. In certain embodiments, the stage two surfactant that has the highest oil recovery test result may be selected as the stage two surfactant. In other embodiments, a predetermined threshold for the oil recovery test result may be compared to the oil recovery test results and only stage two surfactants meeting the predetermined threshold may be identified as the stage two surfactant.

The stage one surfactant and the stage two surfactant may be the same or different. The stage one surfactant may be nonionic, cationic, anionic, zwitterionic, derivatives thereof or combinations thereof. The stage two surfactant may be nonionic, cationic, anionic, zwitterionic, derivatives thereof or combinations thereof.

Examples of nonionic surfactants include, but are not limited to, alcohol oxylalkylates, alkyl phenol oxylalkylates, nonionic esters such as sorbitan esters alkoxylates of sorbitan esters, castor oil alkoxylates, fatty acid alkoxylates, lauryl alcohol alkoxylates, nonylphenol alkoxylates, octylphenol alkoxylates, and tridecyl alcohol alkoxylate, derivatives thereof, and combinations thereof.

Examples of cationic surfactants include, but are not limited to, alkyl amines, alkyl amine salts, quaternary ammonium salts such as trimethyltallowammonium halides (e.g., trimethyltallowammonium chloride, trimethyltallowammonium bromide), amine oxides, alkyltrimethyl amines, triethyl amines, alkyldimethylbenzylamines, cetyltrimethylammonium bromide, alkyl dimethyl benzyl-ammonium chloride, trimethylcocoammonium chloride, derivatives thereof, and combinations thereof.

Examples of anionic surfactants include, but are not limited to, alkyl carboxylates, alkylether carboxylates, N-acylaminoacids, N-acylglutamates, N-acyl-polypeptides, alkylbenzenesulfonates, paraffinic sulfonates, α-olefinsulfonates, lignosulfates, derivatives of sulfosuccinates, polynapthylmethylsulfonates, alkyl sulfates, alkylethersulfates, $C_8$ to $C_{22}$ alkylethoxylate sulfate, alkylphenol ethoxylate sulfate (or salts thereof), monoalkylphosphates, polyalkylphosphates, fatty acids, alkali salts of fatty acids, glyceride sulfates, sodium salts of fatty acids, soaps, derivatives thereof, and combinations thereof.

Examples of amphoteric or zwitterionic surfactants include, but are not limited to, dihydroxyl alkyl glycinate, alkyl ampho acetate or propionate, alkyl betaine, alkyl amidopropyl betaine and alkylimino mono- or di-propionates derived from certain waxes, fats and oils, and combinations thereof.

In certain embodiments, the nonionic, cationic, anionic, and/or zwitterionic surfactant(s) selected according to the methods of the present disclosure may be used in combination with one or more additional surfactants, including but not limited to nonionic, cationic, anionic, and/or zwitterionic surfactant(s), and combinations thereof. Without being bound by theory, the inclusion and/or selection of such surfactants may depend upon, additional experiments or tests performed to evaluate one or more properties of the surfactant and/or its interaction with rock surfaces and/or oil in the subterranean formation.

In another embodiment, fractures are produced using a hydraulic fracturing operation. A portion of a well is hydraulically isolated to focus the injected treatment fluid pressure on an isolated interval, or stage. After isolating the stage, a treatment fluid ("pad fluid") is injected without proppant to initiate and propagate the fracture. A stage one surfactant may be added to the pad fluid as it is injected. Proppant is then added to the treatment fluid to keep the fractures open after pumping. Next, in the flush, treatment fluid without proppant is injected to push any remaining free proppant in the well into the fractures. In this embodiment, the stage two surfactant is added to the treatment fluid. In an alternate embodiment, the stage two surfactant may also be added to the treatment fluid with the stage one surfactant and in the flush. Next, in flowback, the well is allowed to flow, thereby releasing the treatment fluids, formation water, and hydrocarbons. A pre-defined soak time may be incorporated between the flush and the flowback.

Figure 4:
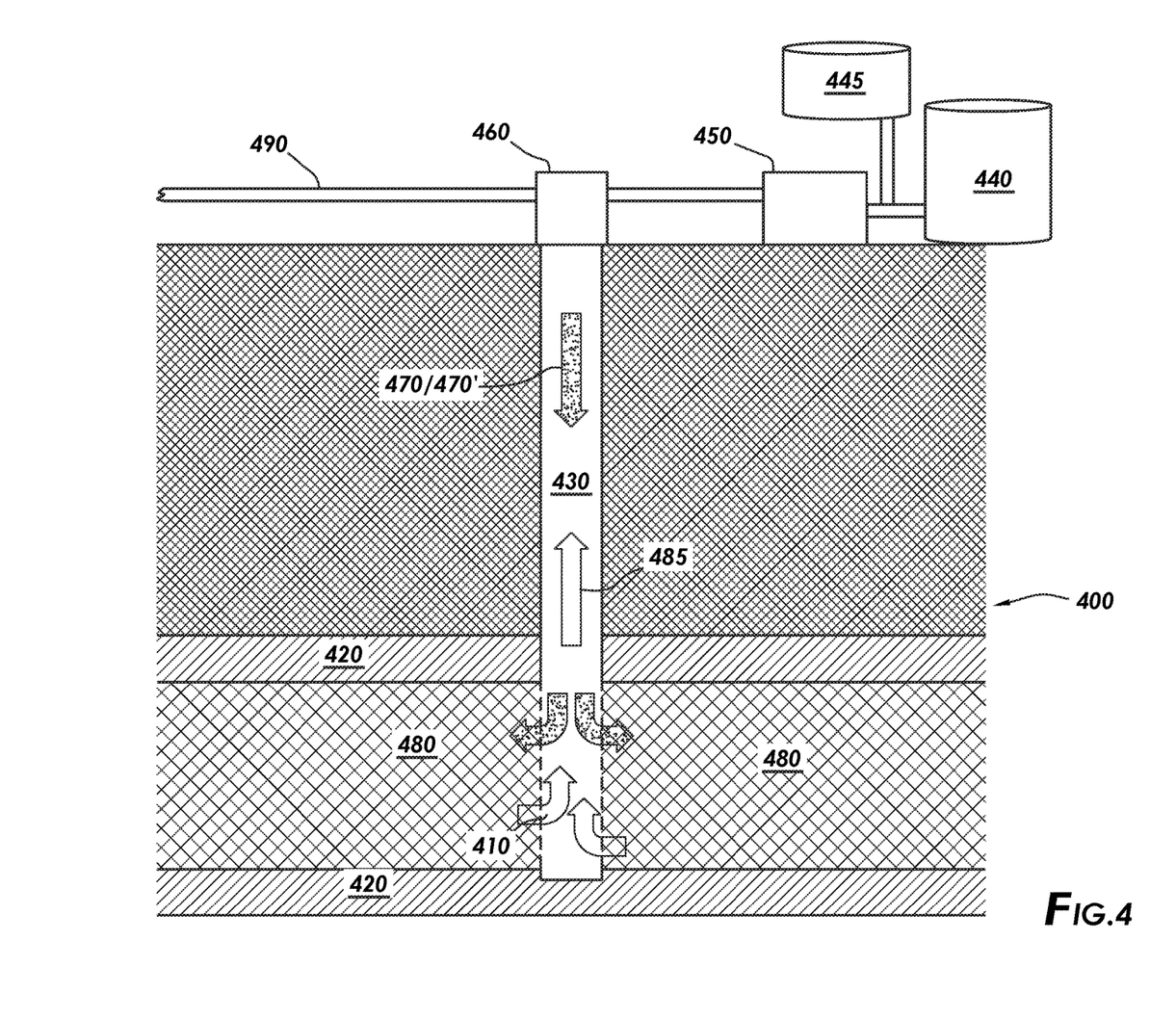
FIG. 4 is a depiction of an oil recovery system consistent with certain embodiments of the present disclosure.

FIG. 4 depicts oil recovery system 400 for enhancing recovery of hydrocarbons, such as oil 410 from low permeability reservoir 420. Bore hole 430 is formed by drilling to the low permeability reservoir 420. In certain embodiments, oil recovery system 400 includes stage one treatment fluid storage tank 440 and stage two treatment fluid storage tank 445 fluidly coupled to pump 450, which is fluidly coupled to wellhead 460. Although only two treatment fluid storage tanks are shown, any number may be used. Stage one fluid storage tank 440 contains stage one treatment fluid containing the stage one surfactant. Stage two fluid storage tank 445 contains stage two treatment fluid containing the stage two surfactant.

Figure 5:
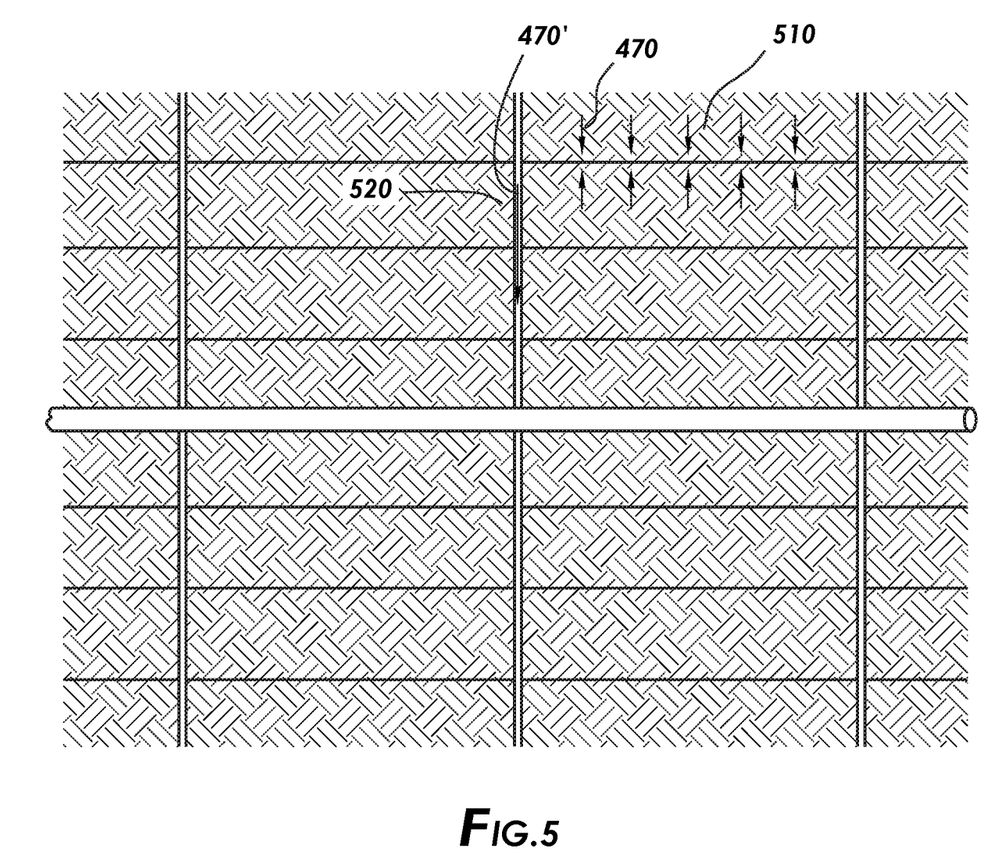
FIG. 5 is a depiction of a fracture network consistent with certain embodiments of the present disclosure.

In inject stage one surfactant 150, stage one treatment fluid 470 is transferred from stage one treatment fluid storage tank 440 to borehole 430 using pump 450. As shown in FIG. 5, stage one treatment fluid 470 enters matrix 510 to enhance the water imbibition into matrix 510, which increases oil flow out of matrix 510 and into the fracture network 520 (as shown in FIG. 5 by "main fracture" and "microfracture."

In inject stage two surfactant 160, stage two treatment fluid 470' is transferred from stage two treatment fluid storage tank 445 to borehole 430 using pump 450. As shown in FIG. 5, stage two treatment fluid 470' enters fracture network 520, which increases oil flow out of fracture network 520 and into borehole 430. In certain embodiments, stage two treatment fluid 470' remains within fracture network 520.

As shown in FIG. 4, oil 410 displaced from reservoir 420 migrates from producing portion 480 of reservoir 420 to borehole 430. Within borehole 430, produced oil 485 moves toward wellhead 460. Produced oil 485 is recovered via the flowline 490.

EXAMPLES

Example 1—Oil Recovery

A shale core plug will be crushed to 80~100 mesh or 149~177 microns to expose the large surfaces in the shale. The crushed core will then be saturated with the crude oil from the production well at the formation temperature. The saturated core will be filtered and dried in a thermal oven.

The saturated core will be packed into a glass column and a stage two treatment fluid containing a stage two surfactant pumped through the column at a fixed flow rate. The effluent will be collected at the exit of the glass column and the oil recovery calculated for each pass by using infrared spectroscopy.

Example 2 Capillary Pressure

Crushed shale core will be loaded into a powder cell and connected to a force transducer. The powder cell will be brought into contact with a stage one treatment fluid containing a stage one surfactant. The weight gain of the powder cell will be recorded as a function of time. The square of weight gain will be plotted against the time. The slopes of the plots will be used to compare the capillary pressure. Typically, the smaller the slopes, the lower the capillary pressure is.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure and that they may make various changes, substitutions, and alterations herein without departing from the spirit and scope of the present disclosure.

What is claimed is:

1. A fluid injection process comprising:
   removing a core sample from a low permeability reservoir;
   performing an imbibition test on a plurality of stage one surfactants, each stage one surfactant mixed with a first treatment fluid, using a portion of the core sample to obtain a wettability index or measurement of capillary pressure for each stage one surfactant;
   selecting a stage one surfactant by determining which of the plurality of stage one surfactants has the highest wettability index or lowest capillary pressure;
   performing an oil recovery test on a plurality of stage two surfactants, each stage two surfactant mixed with a second treatment fluid;
   selecting a stage two surfactant by determining which of the plurality of stage two surfactants has the highest oil recovery test result;
   injecting the selected stage one surfactant into a matrix of the low permeability reservoir; and
   injecting the selected stage two surfactant into a fracture network of the low permeability reservoir.

2. The process of claim 1, wherein the stage one surfactant is different than the stage two surfactant.

3. The process of claim 1, wherein the stage two surfactant is retained within the fracture network.

4. The process of claim 1 further comprising after the step of injecting the selected stage one surfactant into a matrix of the low permeability reservoir:
   increasing oil flow from the matrix.

5. The method of claim 4, further comprising after the step of injecting the selected stage two surfactant into a fracture network of the low permeability reservoir:
   increasing oil flow from the fracture network.

6. The method of claim 5 further comprising after the step of selected stage two surfactant into a fracture network of the low permeability reservoir:
   displacing oil through a borehole drilled within the low permeability reservoir.

7. The method of claim 1, wherein the stage one surfactant is nonionic, cationic, anionic, zwitterionic, or a combinations thereof.

8. The method of claim 1, wherein the stage two surfactant is nonionic, cationic, anionic, zwitterionic, or a combinations thereof.

9. The method of claim 1, wherein the imbibition test is the Amott cell test.

10. The method of claim 1, wherein the step of performing the oil recovery test comprises:
    saturating the cores sample that has been crushed with crude oil from the low permeability reservoir;
    passing the second treatment fluid containing one of the stage two surfactant through the core sample;
    collecting the effluent; and
    quantifying the amount of crude oil in the effluent.

11. The method of claim 1, wherein the first stage surfactant or the second stage surfactant is a nonionic surfactant, wherein the nonionic surfactant is an alcohol oxylalkylate, an alkyl phenol oxylalkylate, a nonionic esters, a castor oil alkoxylate, a fatty acid alkoxylate, a lauryl alcohol alkoxylates, a nonylphenol alkoxylate, a octylphenol alkoxylate, a tridecyl alcohol alkoxylate, or a combination thereof.

12. The method of claim 1, wherein the first stage surfactant or the second stage surfactant is a cationic surfactant, wherein the cationic surfactant is an alkyl amine, an alkyl amine salt, aquaternary ammonium salt, an amine oxide, an alkyltrimethyl amine, a triethyl amine, an alkyldimethylbenzylamine, cetyltrimethylammonium bromide, an alkyl dimethyl benzyl-ammonium chloride, trimethylcoammonium chloride, or combinations thereof.

13. The method of claim 1, wherein the first stage surfactant or the second stage surfactant is an anionic surfactant, wherein the anionic surfactant is an alkyl carboxylate, an alkylether carboxylate, a N-acylaminoacid, a N-acylglutamates, a N-acyl-polypeptides, an alkylbenzenesulfonate, a paraffinic sulfonate, an α-olefinsulfonate, a lignosulfate, a derivative of a sulfosuccinate, a polynapthylmethylsulfonate, an alkyl sulfate, an alkylethersulfate, a $C_8$ to $C_{22}$ alkylethoxylate sulfate, an alkylphenol ethoxylate sulfate or a salt thereof, a monoalkylphosphate, a polyalkylphosphate, a fatty acid, an alkali salt of a fatty acid, a glyceride sulfate, a sodium salt of a fatty acid, a soap or a combinations thereof.

14. The method of claim 1, wherein the first stage surfactant or the second stage surfactant is an amphoteric or zwitterionic surfactant selected from the group consisting of dihydroxyl alkyl glycinate, alkyl ampho acetate or propionate, alkyl betaine, alkyl amidopropyl betaine, alkylimino mono- or di-propionates, and combinations thereof.

* * * * *